(12) United States Patent
Kamata

(10) Patent No.: US 9,146,390 B2
(45) Date of Patent: Sep. 29, 2015

(54) PHOTOCONDUCTIVE ELEMENT, LENS, TERAHERTZ EMISSION MICROSCOPE AND METHOD OF PRODUCING DEVICE

(75) Inventor: Masanao Kamata, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/343,446

(22) PCT Filed: Aug. 28, 2012

(86) PCT No.: PCT/JP2012/005393
§ 371 (c)(1),
(2), (4) Date: Mar. 7, 2014

(87) PCT Pub. No.: WO2013/046534
PCT Pub. Date: Apr. 4, 2013

(65) Prior Publication Data
US 2014/0217288 A1    Aug. 7, 2014

(30) Foreign Application Priority Data

Sep. 30, 2011    (JP) .................................. 2011-216164

(51) Int. Cl.
*G01J 5/20* (2006.01)
*G02B 21/00* (2006.01)
(Continued)

(52) U.S. Cl.
CPC ............... *G02B 21/0016* (2013.01); *G01J 1/42* (2013.01); *G01N 21/63* (2013.01); *G02B 13/14* (2013.01); *G01N 21/3586* (2013.01)

(58) Field of Classification Search
CPC .......... G01J 1/42; G01J 3/42; G01N 21/3586; G01N 21/63; G01N 21/3581; G02B 13/14; G02B 21/0016

USPC ........................................ 250/338.4; 359/356
See application file for complete search history.

(56) References Cited

U.S. PATENT DOCUMENTS 8,067,739 B2 * 11/2011  Itsuji ......................... 250/338.4
2004/0246011 A1 * 12/2004  Tonouchi et al. ............. 324/752
(Continued)

FOREIGN PATENT DOCUMENTS

GB           2484407 A   *   4/2012
JP        2004-219967 A       8/2004
(Continued)

OTHER PUBLICATIONS

Author: Yang et al., Title: A reflected Terahertz-Emission Microscopy, Date:2007, Publisher: Chinese Physical Society and IPO.*

*Primary Examiner* — David J Makiya
*Assistant Examiner* — Taeho Jo
(74) *Attorney, Agent, or Firm* — Sony Corporation

(57) ABSTRACT

[Object] To provide a terahertz emission microscope being capable of improving a detection accuracy of a terahertz electromagnetic wave, a photoconductive element and a lens used therefor, and a method of producing a device.
[Solving Means] A photoconductive element includes a base material, electrodes and a film material. The base material has an incident surface on which a terahertz electromagnetic wave is incident, the terahertz electromagnetic wave generated by irradiating a device to be observed with a pulse laser generated from a light source. The electrodes are formed on the base material and detect the terahertz electromagnetic wave incident on the incident surface of the base material. The film material is formed on the incident surface of the base material, transmits the terahertz electromagnetic wave and reflects the pulse laser.

9 Claims, 3 Drawing Sheets

(51) Int. Cl.
*G01N 21/63* (2006.01)
*G01J 1/42* (2006.01)
*G02B 13/14* (2006.01)
*G01N 21/3586* (2014.01)

(56) References Cited

U.S. PATENT DOCUMENTS

| | | | |
|---|---|---|---|
| 2005/0215031 A1* | 9/2005 | Ouchi | 438/459 |
| 2007/0018634 A1* | 1/2007 | Ohtake et al. | 324/96 |
| 2007/0218376 A1* | 9/2007 | Ouchi | 430/56 |
| 2007/0235650 A1* | 10/2007 | Federici et al. | 250/341.8 |
| 2009/0059205 A1* | 3/2009 | Itsuji | 356/51 |
| 2009/0225311 A1 | 9/2009 | Umetsu | |
| 2009/0225313 A1* | 9/2009 | Umetsu | 356/326 |
| 2010/0013038 A1* | 1/2010 | Ouchi | 257/431 |
| 2011/0109972 A1* | 5/2011 | Ullrich et al. | 359/629 |
| 2011/0215245 A1* | 9/2011 | Ouchi | 250/338.4 |
| 2011/0215246 A1* | 9/2011 | Kajiki | 250/338.4 |
| 2012/0126122 A1* | 5/2012 | Cundiff et al. | 250/338.4 |
| 2012/0326037 A1* | 12/2012 | Ohtake et al. | 250/338.1 |

FOREIGN PATENT DOCUMENTS

| | | | |
|---|---|---|---|
| JP | 4001373 A | | 8/2007 |
| JP | 2007278740 A | * | 10/2007 |
| JP | 2009-210422 A | | 9/2009 |
| JP | 2010-060317 A | | 3/2010 |
| JP | 2010-181288 A | | 8/2010 |
| JP | 4683869 B2 | | 2/2011 |
| JP | 4744604 A | | 5/2011 |
| WO | WO 02060017 A1 | * | 8/2002 |
| WO | WO 2005/022180 A1 | | 3/2005 |
| WO | WO 2006/064653 A1 | | 6/2006 |

\* cited by examiner

PHOTOCONDUCTIVE ELEMENT, LENS, TERAHERTZ EMISSION MICROSCOPE AND METHOD OF PRODUCING DEVICE

TECHNICAL FIELD

The present invention relates to a terahertz emission microscope utilizing a terahertz electromagnetic wave, a photoconductive element and a lens used therefor, and a method of producing a device including the step of observing the device with the terahertz emission microscope.

BACKGROUND ART

A method of inspecting a semiconductor device described in Patent Documents 1, 2, 3 is a non-contact inspection method for a semiconductor device utilizing a terahertz electromagnetic wave. In the inspection method, defects of a semiconductor device are inspected by utilizing a fact that the terahertz electromagnetic wave generated by irradiating the semiconductor device to be inspected with a pulse laser for excitation such as an ultrashort pulse laser is influenced by an electric field distribution and defective wiring within the semiconductor device (for example, Patent Documents 1, 2 and 3).

Within the semiconductor device, a built-in electric field is generated on a pn junction or a surface of a metal semiconductor configuring a MOS (Metal Oxide Semiconductor) transistor even under an unbiased voltage. Accordingly, an inspection apparatus utilizing such a terahertz electromagnetic wave can inspect the defects under an unbiased state, i.e., a non-contact state.

Patent Document 1: Japanese Patent No. 4744604
Patent Document 2: Japanese Patent No. 4001373
Patent Document 3: Japanese Patent No. 4683869

SUMMARY OF INVENTION

When a pulse laser for excitation is reflected, scattered, transmitted etc. on/by/through the device, a detection element for detecting a terahertz electromagnetic wave may be irradiated with the pulse laser. If the detection element includes a semiconductor material, the detection element undesirably generates the terahertz electromagnetic wave, once the detection element is irradiated with the pulse laser. For example, the terahertz electromagnetic wave generated in the device may be faint depending on a type of the device to be inspected. In such a device, it is difficult to separate the terahertz electromagnetic wave generated in the device from the terahertz electromagnetic wave generated in the detection element, thereby decreasing a detection accuracy of the terahertz electromagnetic wave generated in the device.

In view of the above circumstances, an object of the present technology is to provide a terahertz emission microscope being capable of improving the detection accuracy of the terahertz electromagnetic wave, a photoconductive element and a lens used therefor, and a method of producing a device.

Problem to be Solved by the Invention

Means for solving the Problem

In order to achieve the above-described object, the photoconductive element according to the present technology includes a base material, electrodes and a film material.

The base material has an incident surface on which a terahertz electromagnetic wave is incident, the terahertz electromagnetic wave generated by irradiating a device to be observed with a pulse laser generated from a light source.

The electrodes are formed on the base material and detect the terahertz electromagnetic wave incident on the incident surface of the base material.

The film material is formed on the incident surface of the base material, transmits the terahertz electromagnetic wave and reflects the pulse laser.

As the film material that transmits the terahertz electromagnetic wave and reflects the pulse laser is formed on the incident surface of the base material, the generation of the terahertz electromagnetic wave caused by an incidence of the pulse laser on the incident surface of the base material is inhibited. This can improve the detection accuracy of the terahertz electromagnetic wave generated in the device to be observed.

The base material may have the incident surface being different from a surface where the electrodes are formed on the base material. A sampling pulse laser is incident on the surface where the electrodes are formed on the base material. The sampling pulse laser is for detecting the terahertz electromagnetic wave by the photoconductive element at a predetermined timing. Thus, the terahertz electromagnetic wave is incident on the surface that is different from the surface where the electrodes are formed, thereby improving the detection accuracy of the terahertz electromagnetic wave.

The film material may include at least one of an insulator film, a semiconductor film and a conductor film.

A lens according to the present technology includes a lens area and a film material.

The lens area has an incident surface, an exit surface and an inner area. On the incident surface, a terahertz electromagnetic wave is incident. The terahertz electromagnetic wave is generated by irradiating a device to be observed with a pulse laser generated from a light source. The exit surface exits the terahertz electromagnetic wave incident on the incident surface. The inner area guides the terahertz electromagnetic wave between the incident surface and the exit surface.

As the film material that transmits the terahertz electromagnetic wave and reflects the pulse laser is formed on the incident surface of the lens area, the generation of the terahertz electromagnetic wave caused by an incidence of the pulse laser on the incident surface of the base material is inhibited. This can improve the detection accuracy of the terahertz electromagnetic wave generated in the device to be observed.

The lens area may have a curved surface as the incident surface and a flat surface as the exit surface. By disposing the lens area having a such shape, the terahertz electromagnetic wave is collected or collimated and the photoconductive element disposed at an exit surface side of the lens area can effectively detect the terahertz electromagnetic wave.

A terahertz emission microscope according to the present technology includes a light source and a detection element.

The light source emits a pulse laser.

The detection element detects a terahertz electromagnetic wave generated by irradiating a device to be observed with a pulse laser, and has an incident surface and a film material. On the incident surface, the generated terahertz electromagnetic wave is incident. The film material is formed on the incident surface for transmitting the terahertz electromagnetic wave and reflecting the pulse laser.

As the film material that transmits the terahertz electromagnetic wave and reflects the pulse laser is formed on the incident surface of the detection element, the generation of the terahertz electromagnetic wave caused by an incidence of the pulse laser on the incident surface of the base material is inhibited. This can improve the detection accuracy of the terahertz electromagnetic wave generated in the device to be observed.

The light source may generate the terahertz electromagnetic wave having a frequency of $10^{10}$ (Hz) to $10^{14}$ (Hz) by irradiating the device with the pulse laser.

The light source may generate a pulse laser having a wavelength of 2 μm or less and a pulse width of 100 ps or less.

A method of producing a device according to the present technology including the step of inspecting a defect of the device by utilizing a terahertz emission microscope includes generating a pulse laser from a light source.

A terahertz electromagnetic wave is detected by a detection element having an incident surface on which the terahertz electromagnetic wave is incident, the terahertz electromagnetic wave generated by irradiating the device to be observed with a pulse laser, and a film material formed on the incident surface for transmitting the terahertz electromagnetic wave and reflecting the pulse laser.

According to the production method, as the detection accuracy of the detection element is improved as described above, the production method contributes to an improvement of a product quality.

Effect of the Invention

As described above, according to the present technology, the detection accuracy of the detection element can be improved.

MODE(S) FOR CARRYING OUT THE INVENTION

Hereinafter, embodiments of the present technology will be described with reference to the drawings.

[Configuration of Terahelz Emission Microscope]

Figure 1:
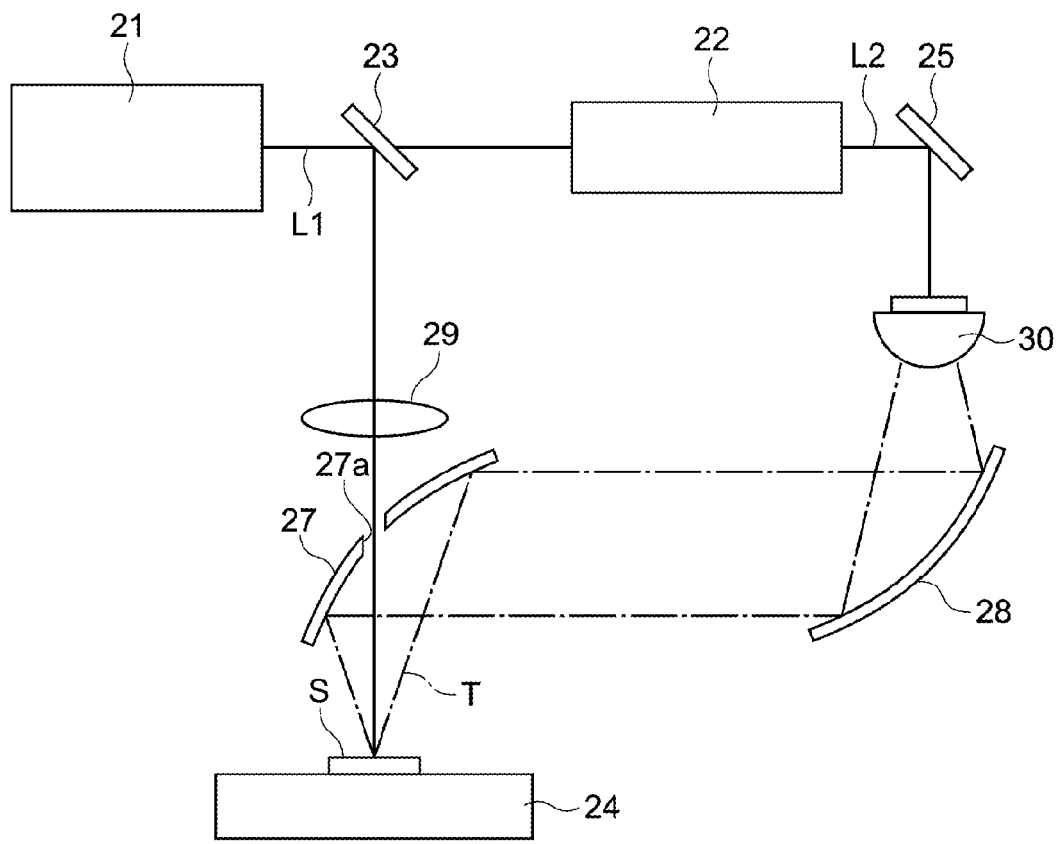
FIG. 1 A diagram schematically and mainly showing an optical system of a terahertz emission microscope according to one embodiment of the present technology.

FIG. 1 is a diagram schematically and mainly showing an optical system of a terahertz emission microscope according to one embodiment of the present technology.

A terahertz emission microscope 100 includes an excitation light source 21, a half mirror 23, a light collection lens 29, an optical delay path 22, a reflection mirror 25, a detection element 30, a pair of parabolic mirrors 27, 28, a stage 24 and the like.

The excitation light source 21 generates an excitation pulse laser for exciting a device to be observed or inspected (hereinafter referred to as "a target device S") disposed on the stage 24. As the excitation light source 21, an ultrashort pulse laser having a wavelength of 2 μm or less and a pulse width of 100 ps or less is used.

The half mirror 23 reflects a part of a pulse laser L1 generated from the excitation light source 21, and guides the reflected light to the light collection lens 29. The pulse laser transmitted through the half mirror 23 is incident on the optical delay path 22.

The collection lens 29 guides the reflected light from the half mirror 23 to the target device S on the stage 24. The target device S is typically a semiconductor device mainly using a semiconductor material such as a light emission device, e.g., a semiconductor laser, a light emission diode, or the like.

The detection element 30 is an element for detecting a terahertz electromagnetic wave (hereinafter referred to as "a terahertz wave T") generated in the target device S.

The pulse laser transmitted through the half mirror 23 is incident on the optical delay path 22. The optical delay path 22 generates a sampling pulse laser L2 for detecting the terahertz wave T with the detection element 30 at any timing. In addition, the optical delay path 22 reflects the generated sampling pulse laser L2 at the reflection mirror 25 such that the sampling pulse laser L2 is incident on the detection element 30.

Typically, the optical delay circuit 22 variably controls an optical length of a pulse laser at a regular interval using a movement mechanism (for example, a movement stage) for moving a mirror (not shown) and the like. An arrival time of the laser pulse to the detection element 30 depends on its optical path length. As a result, the optical delay path 22 can output the sampling pulse laser L2 at a predetermined timing.

The pair of parabolic mirrors 27, 28 guide the terahertz wave T generated in the target device S to the detection element 30. One parabolic mirror 27 of the pair has a hole 27a through which the pulse laser collected by the light collection lens 29 passes.

[Configuration of Detection Element]

Figure 2:
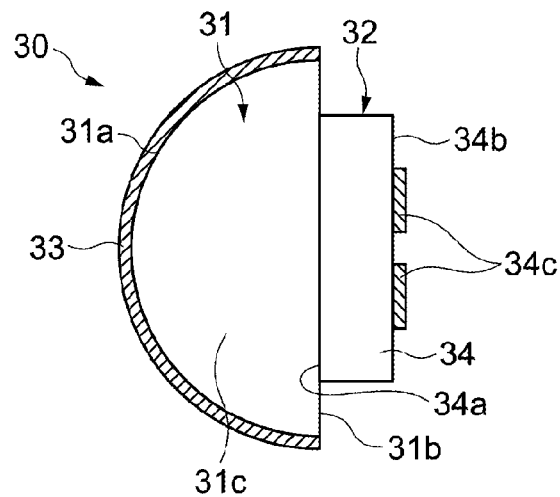
FIG. 2 A side diagram showing a detection element.

FIG. 2 is a side diagram showing the detection element 30.

The detection element 30 includes a photoconductive element (a photoconductive antenna (PCA)) 32 and a lens 31 mounted thereon.

The photoconductive element 32 has a known structure, and includes a substrate 34 that will be the base material, and electrodes 34c formed on the substrate 34, for example. These electrodes 34c are disposed apart from each other such that a minor space is left between the electrodes 34c to form an antenna. In addition, a photoconductive film (not shown) is formed on the substrate 34. When the photoconductive film is irradiated with excitation light, photocarriers are generated. The substrate 34 is typically made of a semiconductor material such as a GaAs based material, but is not limiting thereto. The above-described sampling pulse laser L2 is incident on a surface 34b where the electrodes 34c are formed of the substrate 34. The terahertz wave T from the target device S is incident on a surface 34a at a lens 31 side being different from and opposite to the surface 34b via the lens 31 according to this embodiment.

The lens 31 includes an incident surface (a curved surface) 31a formed curved, an exit surface (a flat surface) 31b formed flat, and an inner area 31c that guides the terahertz wave T between the incident surface 31a and the exit surface 31b, for example. In other words, the lens 31 is a convex lens and typically has a hemispherical shape. The incident surface 31a, the inner area 31c and the exit surface 31b form a lens area. The substrate 34 is adhered to the exit surface 31b of the lens 31. Specifically, the surface 34a of the substrate 34 is adhered to the exit surface 31b of the lens 31.

The shape of the lens 31 is not limited to the hemispherical shape, and may be a part of the hemisphere shape, an aspherical shape, a Fresnel lens shape, or the like. In other words, the lens 31 may have any shape so long as the photoconductive element 32 can effectively detect the terahertz wave T.

Depending on an amplitude of the terahertz wave T generated in the target device S, a current flowing between the electrodes 34c (or a voltage between the electrodes 34c) is changed. The terahertz emission microscope 100 measures the current (or the voltage) between the electrodes 34c at the timing that the sampling pulse laser L2 is incident on the detection element 30 while the terahertz wave T is incident between the electrodes 34c on the substrate 34 via the lens 31. In this way, the terahertz emission microscope 100 can acquire an amplitude value of the terahertz wave T for each timing as a waveform.

A film material 33 is formed on the incident surface 31a of the lens 31. The film material 33 is designed such that the terahertz wave T generated in the target device S is transmitted and guides to the incident surface 31a of the lens 31, and the pulse laser L1 reflected, scattered, transmitted etc. on/by/through the target device S is reflected. Once the photoconductive element 32 is irradiated with the pulse laser, the terahertz wave T is generated by optical Denver effect etc. as the photoconductive element 32 is made of a semiconductor material or a conductive material.

In particular, when the target device S is a light emission device such as a semiconductor laser, a light emission diode and the like, the device is often designed such that a thickness direction of the device is the same as or similar to a direction of an internal electric field of a pn junction of the device. It may cause the following problem: In other words, a direction of a dipole moment that originates the terahertz wave becomes the thickness direction of the device, which results that most of the terahertz wave emitted therefrom is undesirably confined to inside of the substrate 34 by total reflection. Therefore, the terahertz wave emitted from the device will be extremely smaller than that emitted from the device having the dipole moment in parallel with a surface of the device. Accordingly, it will be difficult to separate the terahertz wave T generated in the target device S from the terahertz wave generated in the photoconductive element 32 (or the detection element 30 when the lens 31 is a silicon lens), thereby decreasing a detection accuracy of the terahertz wave T generated in the target device S. In other words, an S/N ratio is undesirably low.

In view of the above, there may be another plan that a transparent conductive film coated substrate that reflects the terahertz wave and transmits the ultrashort pulse laser is disposed within the optical system of the terahertz emission microscope 100, thereby preventing the detection element 30 from irradiating with the ultrashort pulse laser. However, a reflectance loss of the ultrashort pulse laser is caused by the transparent conductive film coated substrate, the S/N ratio will eventually be undesirably low if an available laser output is limited.

For solving the problem, according to the present technology, the film material 33 is coated on the incident surface 31a of the lens 31 in order to reflect the pulse laser that causes a generation of the terahertz wave from the photoconductive element 32. As a result, the detection accuracy of the terahertz wave T generated in the target device S to be detected can be improved.

For example, the film material 33 includes at least one film of a dielectric film of $SiO_2$, SiN etc., a semiconductor film of Si, GaAs etc. and a metal film of Al, Cu etc. In other words, the film material 33 may be any of a monolayer film or a multi-layer film. It should be appreciated that the material of the film material 33 is not limited thereto.

The film material 33 is formed by a film forming process such as vapor deposition and sputtering, for example. A designer simulates an optical multilayer thin film based on a wavelength to be reflected and a desirable reflectance of the pulse laser, and designs a film thickness, a film number and the material of the film material 33. In order to avoid the generation of the terahertz wave on the film material 33 by the pulse laser, all material is ideally dielectric. It is not necessary to limit to the dielectric as long as a generation amount of the terahertz wave T is low. In other words, the S/N ratio of the signal detected by the detection element 30 may only be provided to an extent that can detect the terahertz wave T from the target device S to be detected.

[Action of Terahertz Emission Microscope]

The excitation light source 21 generates the ultrashort pulse laser having a wavelength of 2 μm or less and a pulse width of 100 ps or less. When the target device S is irradiated with the pulse laser, the target device S generates the terahertz wave T having a frequency of $10^{10}$ (Hz) to $10^{14}$ (Hz), for example.

Specifically, when the pulse laser is incident on the target device S, free electrons are generated within the target device S. By accelerating the free electrons by the internal electric field of the target device S, a transient current is generated. When the transient current induces dipole emission, the terahertz wave T is emitted.

The terahertz emission microscope 100 compares the stored information about the terahertz wave detected by the detection element 30 upon normal time to the information about the terahertz wave T generated in the target device S upon inspection, thereby inspecting presence or absence of defects (presence or absence of abnormalities). For example, if the internal electric field of the target device S is abnormal or the target device S has defective wiring, the terahertz wave T thus obtained changes from a normal value. Specifically, the wiring of the target device S functions as an antenna. If the wiring is defective, the terahertz wave T being different from normal time is emitted.

A part of the pulse laser not absorbed by the target device S is reflected (scattered and transmitted as well) on the target device S and is guided to the detection element 30. However, according to the present technology, the film material 33 is formed on the incident surface 31a of the lens 31 in the detection element 30, thereby inhibiting the generation of the terahertz wave on the detection element 30. This will enable the S/N ratio to be high by the detection element 30, and the detection accuracy of the terahertz wave T generated in the target device S to be high.

In addition, according to this embodiment, there is no need to dispose the transparent conductive film coated substrate that transmits the ultrashort pulse laser, as described above. Therefore, component counts will be reduced to achieve a smaller sized terahertz emission microscope.

Detection Element According to Another Embodiments

Another Embodiment 1

Figure 3:
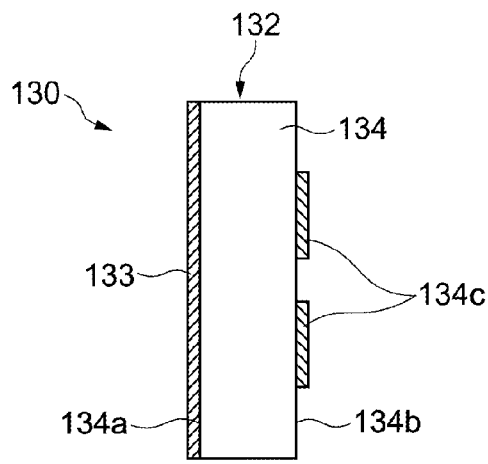
FIG. 3 A side diagram showing a detection element according to another embodiment.

FIG. 3 is a side diagram showing a detection element according to another embodiment. In the following description, the description about similar members, functions etc. according to the embodiment shown in FIGS. 1 and 2 is simplified or omitted, and different points will be mainly described.

A detection element 130 according to this embodiment includes a photoconductive element 132 shown in FIG. 2 and no lens 31 shown in FIG. 2. Since the lens mainly has the functions to collect, collimate or effectively detect the terahertz wave incident on the photoconductive element, the lens is not essential.

In this embodiment, on a substrate 134 of the photoconductive element 132, at an opposite side of a forming surface 134b of electrodes 134c, an incident surface 134a on which the terahertz wave T is incident is formed. On the incident surface 134a, a film material 133 that transmits the terahertz wave T and reflects the pulse laser is formed. The material of the film material 133 can be selected as appropriate, as described above.

Another Embodiment 2

Figure 4:
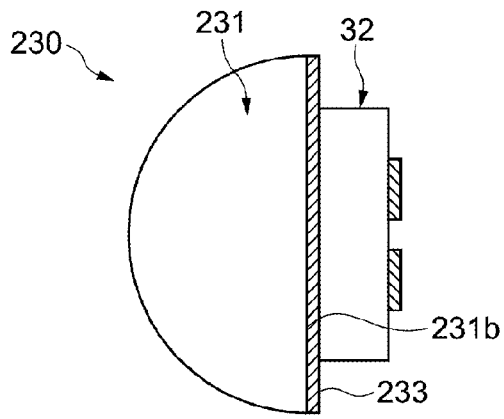
FIG. 4 A side diagram showing a detection element according to still another embodiment.

FIG. 4 is a side diagram showing a detection element according to still another embodiment. In a detection element 230, a film material 233 described above that transmits the terahertz wave T and reflects the pulse laser is formed on an exit surface 231b that is at a flat surface side of the lens 231.

EXAMPLE

Figure 5:
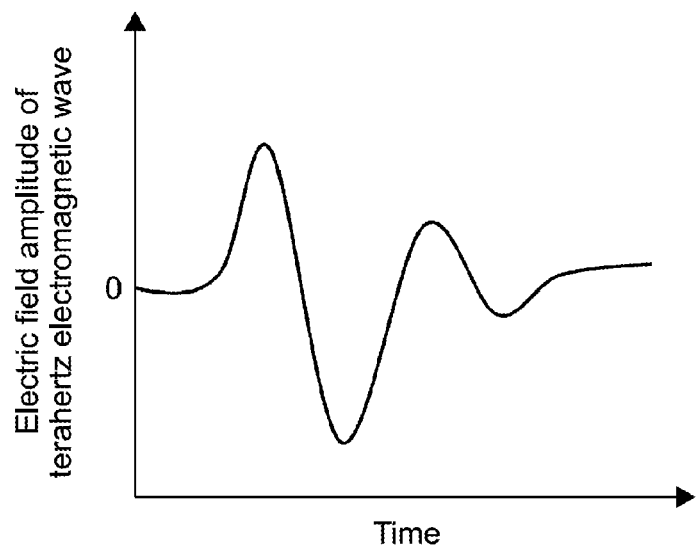
FIG. 5 A graph showing a detection signal of the detection element having a lens where no film material is formed.

FIG. 5 is a graph showing a detection signal of the detection element having a hemispherical lens where no film material is formed. The present inventor detected the terahertz wave using the detection element having a hemispherical lens where no film material is formed (a detection element having no film material 33 in FIG. 2). In the embodiment, a measurement was carried out under the condition that no terahertz emission was generated from the target device by irradiating a spot where no target device was mounted within one product to be inspected with a laser pulse. In other words, the graph shown in FIG. 5 shows not the terahertz wave from the target device, but the terahertz wave generated substantially only on the detection element.

In this embodiment, as the ultrashort pulse laser generated from the excitation source 21, a titanium sapphire femtosecond laser having a repetitive frequency of 80 MHz, a center wavelength of 800 nm and a pulse width of 100 ps was used. As the photoconductive element of the detection element where no film material is formed, a bowtie antenna photoconductive element having a sensitivity for an electromagnetic wave having a frequency between 0.1 THa to 5 THz was used.

Figure 6:
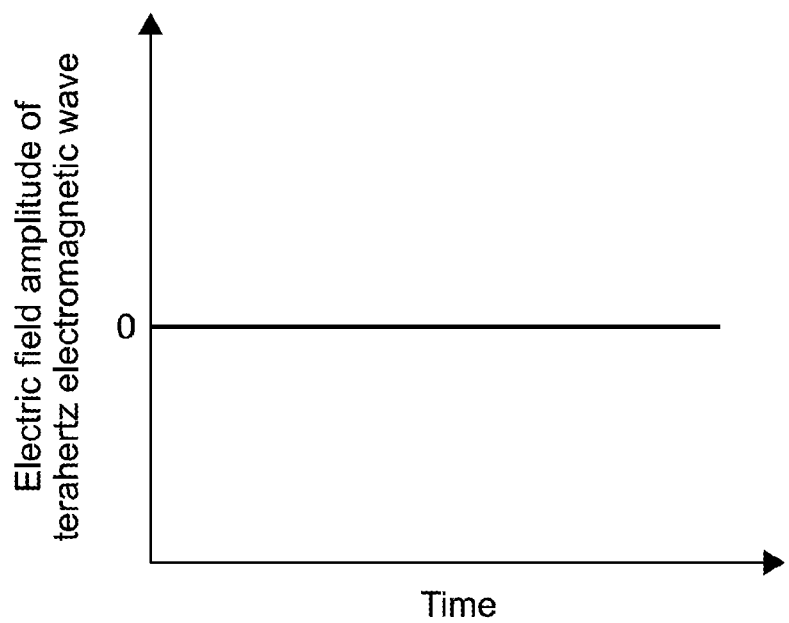
FIG. 6 A graph showing an expected detection signal when the detection element according to the present technology is used.

In contrast, when the detection element 30 where the film material 33 is formed is used, for example, in the embodiment shown in FIG. 2, it is expected that the detection element 30 almost does not detect the terahertz wave from the product to be inspected, as shown in FIG. 6. In other words, it is expected that the detection element 30 substantially does not detect the terahertz wave generated on the detection element 30.

Other Embodiments

The present technology is not limited to the above-described embodiments, and other various embodiments can be possible.

The terahertz emission microscope 100 according to the embodiment shown in FIG. 1 has the optical system where the terahertz wave T generated from the pulse laser at an incident side (at a surface side) of the target device S is guided by the parabolic mirrors 27, 28 to the detection element 30. However, the terahertz wave T is also generated at a rear side of the target device S from the pulse laser incident on the target device S (in fact, the terahertz wave T is generated omnidirectionally 360° around). The terahertz wave generated at the rear side transmits the stage 24. In view of this, the optical system including the detection element 30, 132 or 320 may be disposed at the rear side of the target device S.

For example, by combining the configurations shown in FIGS. 2 and 4, the film material may be formed substantially all over the lens.

In the above-described embodiments, the substrate is used as the base material of the photoconductive element 32. The base material is not limited to a thin plate element, but also may have a rectangular parallelepiped, a regular hexahedron, a rectangular column, a cylinder or any other shapes. In this case, the incident surface of the base material on which the terahertz electromagnetic wave is incident is not limited to the surface at the opposite side of the electrode forming surface of the base material, but may be any surface being different from the electrode forming surface.

Otherwise, it is possible to combine at least two characteristic features among the characteristic features in the above-described respective embodiments.

The present technology may have the following configurations.

(1) A photoconductive element, including:
  a base material having an incident surface on which a terahertz electromagnetic wave is incident, the terahertz electromagnetic wave generated by irradiating a device to be observed with a pulse laser generated from a light source;
  electrodes formed on the base material for detecting the terahertz electromagnetic wave incident on the incident surface of the base material; and
  a film material formed on the incident surface of the base material for transmitting the terahertz electromagnetic wave and reflecting the pulse laser.

(2) The photoconductive element according to (1) above, wherein the base material has the incident surface being different from a surface where the electrodes are formed on the base material.

(3) The photoconductive element according to (1) or (2) above, wherein the film material includes at least one of an insulator film, a semiconductor film and a conductor film.

(4) A lens, including:
  a lens area having an incident surface on which a terahertz electromagnetic wave is incident, the terahertz electromagnetic wave generated by irradiating a device to be observed with a pulse laser generated from a light source, an exit surface for exiting the terahertz electromagnetic wave incident on the incident surface, and an inner area for guiding the terahertz electromagnetic wave between the incident surface and the exit surface; and
  a film material formed on at least one of the incident surface and the exit surface for transmitting the terahertz electromagnetic wave and reflecting the pulse laser.

(5) The lens according to (4) above, wherein the lens area has a curved surface as the incident surface and a flat surface as the exit surface.

(6) A terahertz emission microscope, including:
  a light source for emitting a pulse laser; and
  a detection element for detecting a terahertz electromagnetic wave generated by irradiating a device to be observed with a pulse laser, the detection element having an incident surface on which the generated terahertz electromagnetic wave is incident, and a film material formed on the incident surface for transmitting the terahertz electromagnetic wave and reflecting the pulse laser.

(7) The terahertz emission microscope according to (6) above, wherein the light source generates the terahertz electromagnetic wave having a frequency of $10^{10}$ (Hz) to $10^{14}$ (Hz) by irradiating the device with the pulse laser.

(8) The terahertz emission microscope according to (6) or (7) above, wherein the light source generates a pulse laser having a wavelength of 2 μm or less and a pulse width of 100 ps or less.

(9) A method of producing a device including the step of inspecting a defect of the device by utilizing a terahertz emission microscope, including:
generating a pulse laser from a light source; and
detecting a terahertz electromagnetic wave by a detection element having an incident surface on which the terahertz electromagnetic wave is incident, the terahertz electromagnetic wave generated by irradiating the device to be observed with a pulse laser, and a film material formed on the incident surface for transmitting the terahertz electromagnetic wave and reflecting the pulse laser.

DESCRIPTION OF SYMBOLS 1 pulse laser L1
21 excitation light source
30, 130, 230 detection element
31, 231 lens
31a incident surface
31b, 231b exit surface
31c inner area
32, 132 photoconductive element
33, 133, 233 film material
34, 134 substrate
34c, 134c electrode
100 terahertz emission microscope
134a incident surface

The invention claimed is:

1. A photoconductive element, comprising:
a base material having an incident surface on which a terahertz electromagnetic wave is incident, the terahertz electromagnetic wave generated by irradiating a device to be observed with a pulse laser generated from a light source;
electrodes formed on the base material for detecting the terahertz electromagnetic wave incident on the incident surface of the base material; and
a film material formed on the incident surface of the base material for transmitting the terahertz electromagnetic wave and reflecting the pulse laser.

2. The photoconductive element according to claim 1, wherein the base material has the incident surface being different from a surface where the electrodes are formed on the base material.

3. The photoconductive element according to claim 1, wherein the film material includes at least one of an insulator film, a semiconductor film and a conductor film.

4. A lens, comprising:
a lens area having an incident surface on which a terahertz electromagnetic wave is incident, the terahertz electromagnetic wave generated by irradiating a device to be observed with a pulse laser generated from a light source, an exit surface for exiting the terahertz electromagnetic wave incident on the incident surface; and
an inner area for guiding the terahertz electromagnetic wave between the incident surface and the exit surface; and
a film material formed on at least one of the incident surface and the exit surface for transmitting the terahertz electromagnetic wave and reflecting the pulse laser.

5. The lens according to claim 4, wherein the lens area has a curved surface as the incident surface and a flat surface as the exit surface.

6. A terahertz emission microscope, comprising:
a light source for emitting a pulse laser; and
a detection element for detecting a terahertz electromagnetic wave generated by irradiating a device to be observed with a pulse laser, the detection element having an incident surface on which the generated terahertz electromagnetic wave is incident, and a film material formed on the incident surface for transmitting the terahertz electromagnetic wave and reflecting the pulse laser.

7. The terahertz emission microscope according to claim 6, wherein the light source generates the terahertz electromagnetic wave having a frequency of $10^{10}$ (Hz) to $10^{14}$ (Hz) by irradiating the device with the pulse laser.

8. The terahertz emission microscope according to claim 6, wherein the light source generates a pulse laser having a wavelength of 2 μm or less and a pulse width of 100 ps or less.

9. A method of producing a device comprising the step of inspecting a defect of the device by utilizing a terahertz emission microscope, comprising:
generating a pulse laser from a light source; and
detecting a terahertz electromagnetic wave by a detection element having an incident surface on which the terahertz electromagnetic wave is incident, the terahertz electromagnetic wave generated by irradiating the device to be observed with a pulse laser, and a film material formed on the incident surface for transmitting the terahertz electromagnetic wave and reflecting the pulse laser.

* * * * *